United States Patent [19]

Weinstein et al.

[11] 4,188,118
[45] Feb. 12, 1980

[54] MANIPULATOR FOR ROTATING AND EXAMINING SMALL SPHERES

[75] Inventors: Berthold W. Weinstein; David L. Willenborg, both of Livermore, Calif.

[73] Assignee: The United States of America as represented by the United States Department of Energy, Washington, D.C.

[21] Appl. No.: 906,815

[22] Filed: May 17, 1978

[51] Int. Cl.² .................. G01N 21/16; G01N 21/32
[52] U.S. Cl. .................................. 356/244; 250/442; 250/491; 356/237; 356/240
[58] Field of Search ................ 356/237, 239, 240, 244; 250/442, 456, 491

[56] References Cited

U.S. PATENT DOCUMENTS 3,342,994   9/1967   Franken et al. .................. 250/442

Primary Examiner—Vincent P. McGraw
Attorney, Agent, or Firm—R. V. Lupo; Roger S. Gaither; L. E. Cunningham

[57] ABSTRACT

A manipulator which provides fast, accurate rotational positioning of a small sphere, such as an inertial confinement fusion target, which allows inspecting of the entire surface of the sphere. The sphere is held between two flat, flexible tips which move equal amounts in opposite directions. This provides rolling of the ball about two orthogonal axes without any overall translation. The manipulator may be controlled, for example, by an x- and y-axis driven controlled by a mini-computer which can be programmed to generate any desired scan pattern.

6 Claims, 8 Drawing Figures

MANIPULATOR FOR ROTATING AND EXAMINING SMALL SPHERES

BACKGROUND OF THE INVENTION

The invention described herein was made at the Lawrence Livermore Laboratory in the course of, or under, Contract No. W-7405-ENG-48 between the United States Department of Energy and the University of California.

The invention relates to the fabrication of inertial confinement fusion targets, particularly to manipulation of spherical members used in such targets for inspection thereof, and more particularly to a manipulator for rotating a small spherical member to any orientation for inspection of the surface thereof.

One of the significant problems associated with the production of targets for inertial confinement fusion applications is the precise manipulation of the tiny hollow glass and metal shells, used as fuel containers, for purposes of examination of thickness, surface roughness, etc. For the characterization of the surface or thickness of these tiny spheres (50 to 500 $\mu m$ diameter) one requires a method of inspecting the entire surface area of the tiny sphere with fast, repeatable positioning thereof.

Vacuum chucks are the conventional tool used for such manipulation, but these have several drawbacks in that a fairly complex two-axis angular manipulator is needed to position the sphere for examination, and it is difficult to align the two axes of rotation with each other and with the center of the sphere. In order to inspect the entire surface, the sphere must be transferred from one chuck to another at least once in examining the entire exterior surface and sphere interior, and with this operation the chuck can mar the sphere surface.

SUMMARY OF THE INVENTION

The present invention overcomes the above-mentioned difficulties associated with the use of vacuum chucks for manipulation of microspheres by using two flexible supportive, parallel membranes or members having flat surfaces, each attached to the end of a hollow capillary tube and containing a sphere to be examined therebetween. The capillary tubes are mounted in manipulators which may synchronously move the tubes, and hence the membranes, in two perpendicular directions parallel to the flat surface of the membranes. As the flat surfaces translate in opposite directions by the same amount, the sphere held therebetween rolls in response, but the sphere center remains fixed. Thus, optical examination of the entire sphere surface and interior is easily performed-in place-by merely moving the membranes appropriately in their own planes.

Therefore, it is an object of this invention to provide a manipulator for tiny spherical members.

A further object of the invention is to provide a manipulator for spheres which allows the entire surface thereof to be examined without marring the surface.

Another object of the invention is to provide a manipulator for microspheres which utilizes two flat, pliable surfaces in frictional contact with a sphere placed therebetween.

Another object of the invention is to provide means for allowing full examination of the interior and exterior surface of tiny spheres by use of a manipulator incorporating a pair of flat surfaces between which the sphere is held, such that as the surfaces are translated, the sphere rolls between them, without translation of its center.

Other objects of the invention will become readily apparent from the following detailed description and accompanying drawings.

DETAILED DESCRIPTION OF PREFERRED EMBODIMENT

The invention involves a simple manipulator for rapidly rotating a tiny sphere or microsphere (50 to 500 $\mu m$) to any orientation for inspection of the exterior surface and interior thereof. The manipulator provides fast, repeatable positioning of the tiny sphere. The microsphere is held between two small, flat surfaces and rolls as the surfaces are moved differentially parallel to one another. The microspheres may, for example, be tiny hollow glass or metal shells used in the fabrication of inertial confinement fusion targets. The invention is not limited to any specific size of spheres as it can be effectively utilized for spheres larger or smaller than those exemplified above, where a requirement exists for inspecting the entire surface area of a sphere with fast, repeatable positioning.

Basically, the manipulator arm of this invention consists of a pair of flat, pliable surfaces at the ends of small capillary tubes, the microsphere being held between the two surfaces. The capillary tubes are mounted in a manipulator arm mechanism so that they are movable in two directions parallel to the surfaces by an x- and y-axis driver, for example, such as described and claimed in copending U.S. patent application Ser. No. 906,818, filed May 17, 1978, now U.S. Pat. No. 4,157,490, issued June 5, 1979, in the name of B. W. Weinstein and assigned to the assignee of this application and incorporated herein by reference. As the surfaces are translated, the microsphere rolls between them. If the two surfaces are moved simultaneously in opposite directions, the microsphere does not move, but simply rolls about its center. Translation in two directions provides rolling about two orthogonal axes.

Figure 1:
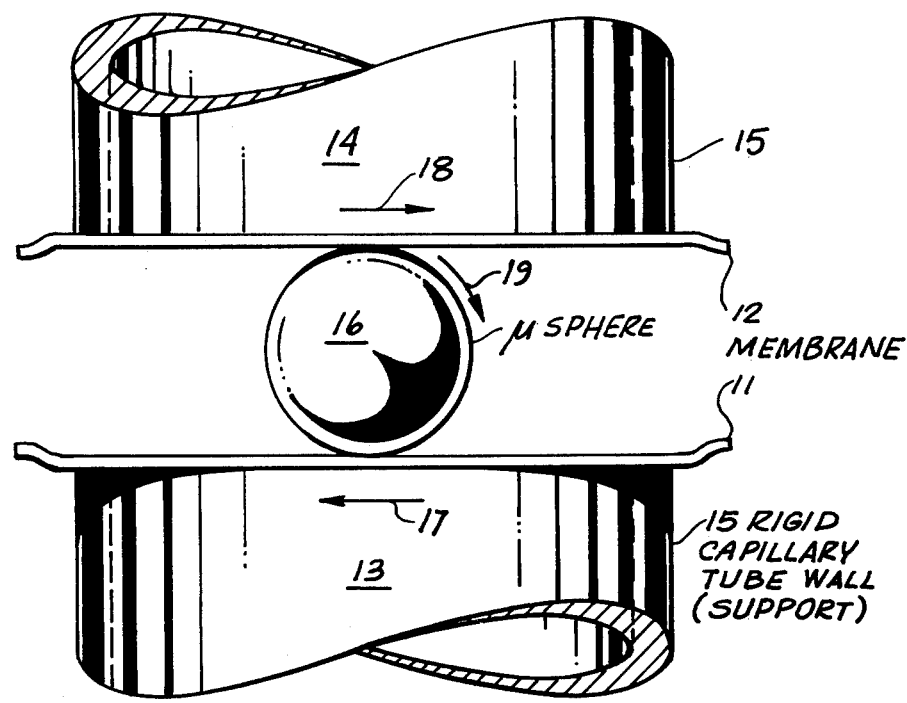
FIG. 1 schematically illustrates an enlarged view of a portion of an embodiment of a manipulator made in accordance with the invention.
Figure 5A:
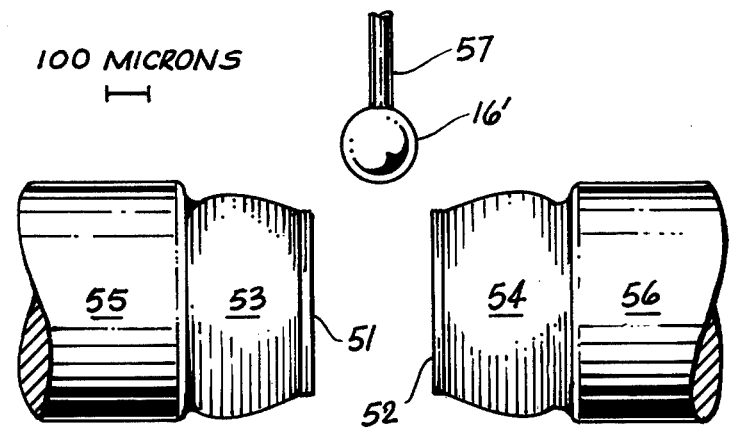
FIGS. 5a-5c partially illustrate the operational sequence of another embodiment of the manipulator.
Figure 5B:
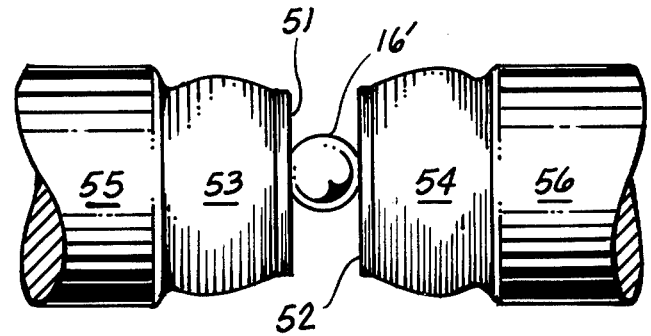

Referring now to the drawings, FIG. 1 illustrates an embodiment wherein two flexible, supportive, parallel tips or membranes 11 and 12 are attached to respective ends of hollow capillary tubes or members 13 and 14 having a rigid wall 15 for support, and retaining a sphere or microsphere ($\mu$sphere) 16 between the membranes 11 and 12. The capillary tubes 13 and 14 are mounted in manipulator arms, as in FIGS. 5a-5c, controlled via an x- and y- axis driver, not shown, which may synchronously move the tubes, and hence the membranes 11 and 12, in two perpendicular directions parallel to the membrane surfaces. As the membranes 11 and 12 translate in opposite directions by the same amount, indicated by arrows 17 and 18, such movement causes the μsphere 16 to roll as indicated by arrow 19, but the μsphere center remains fixed. Thus, optical or x-ray examination of the entire μsphere is easily performed-in place-by merely moving the membranes 11 and 12 appropriately in their own planes. The manipulator arms may be controlled, for example, by the driver mechanism of the above referenced co-pending application via a mini-computer, not shown, having X-Y stages, which can be programmed to generate any desired scan pattern of the μsphere.

Figure 2:
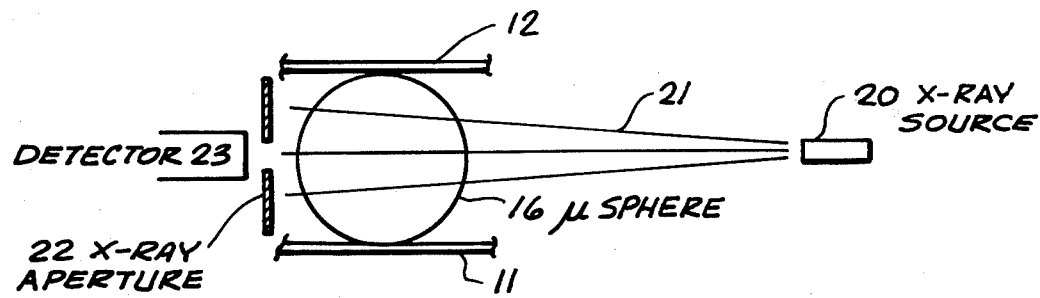
FIG. 2 schematically illustrates the FIG. 1 embodiment in combination with an x-ray examination mechanism.
Figure 3:
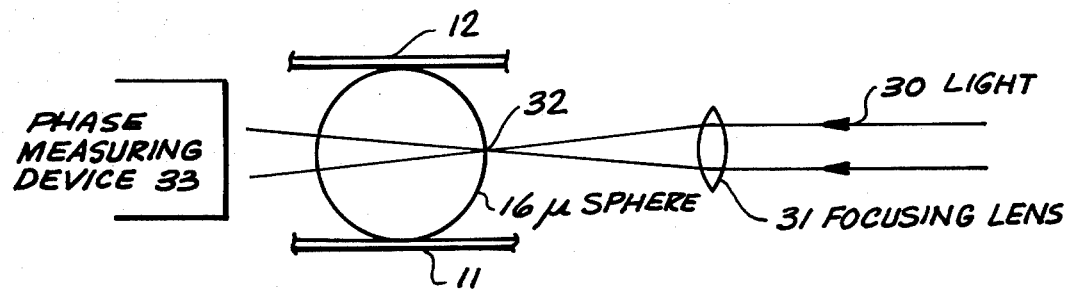
FIG. 3 schematically illustrates the FIG. 1 embodiment in combination with a light examination mechanism.

The μspheres can be examined by x-ray absorption, or light transmission interference, as illustrated in FIGS. 2 and 3; or reflection interferometry or a scanning electron microscope may also be used to examine the surface of the microsphere where it is optically opaque.

FIG. 2 illustrates an apparatus using x-ray absorption for examination of a microsphere and consists of an x-ray source 20 directing a beam of x-rays 21 through μsphere 16, retained by membranes 11 and 12, which pass through an x-ray aperture 22 onto a detector 23. The x-ray examination apparatus is known in the art and inasmuch as such does not constitute part of the present invention further description thereof is unnecessary. However, it is readily apparent that as μsphere 16 is rolled as described above, the entire sphere may be examined.

The apparatus of FIG. 3 illustrate optical examination of μsphere 16 using transmission interference wherein a beam of light 30 from a source not shown is directed through a focusing lens 31 onto a spot 32 on μsphere 16 which passes through the μsphere onto a phase measuring device 33. The technique and apparatus for optical examination are known in the art and further description thereof is deemed unnecessary. As in the x-ray examination of FIG. 2, rotation of μsphere 16 by membranes 11 and 12 enables full examination thereof.

By way of example, membranes 11 and 12 may be constructed of Parylene, Mylar, Formvar (manufactured by Union Carbide Corporation, E. I. DuPont DeNemours and Company, and Monsanto Chemical Company, respectively), or cellulose nitrate, or other plastic sheets, such as ordinary household plastic wrap having a thickness of 0.5 μm to 20 μm, and glued over the ends of the hollow capillary tubes. The membrane forms, in each case, sufficient frictional contact to roll the μsphere without slippage thereof between the membranes so that accurate repositioning and even numerical control of the μsphere position is possible. The capillary tubes, for example, may be constructed of glass, plastic, or metal, having an outer diameter (O.D.) of 100 μm to 1 cm, and a wall thickness of 10 μm to 1 mm.

Figure 4:
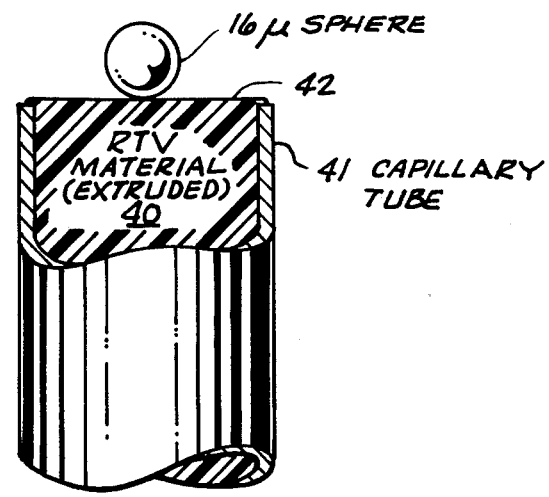
FIG. 4 is an enlarged cross-sectional view of another embodiment of a manipulator arm member made in accordance with the invention.

In place of the membranes of the FIG. 1 embodiment flexible material extruded from the end of a capillary tube and formed into a flat, smooth face may be used. The extruded material can be, for example, room temperature vulcanizing silicone rubber, urethane or butyl rubber, or a silicone adhesive. To form the smooth, flat face at the end of the tip, the material can, for example, be extruded against a smooth, flat surface coated with a release agent. The smooth, flat surface, for example, may be a glass microscope slide, or a polished metal, plastic, or glass surface. FIG. 4 illustrates this approach wherein RTV material 40 is extruded from the end of a capillary tube 41 and formed to provide a smooth, flat, flexible surface or tip 42 for retaining a μsphere 16, only one tube and tip being shown. One problem occasionally encountered with certain of the extrudable materials, as in the FIG. 4 embodiment, is the tendency of the flat surface which contacts the μsphere to develop tracks or grooves as a result of the pressure exerted by the rolling μsphere. Such tracks can be suppressed or eliminated by attachment of a foil or other pliable firm surface to the extruded face across which the microsphere moves.

When the above-described manipulators are used in a scanning electron microscope (SEM), the flat rolling surfaces are coated with a thin (1 nm to 10 nm thickness) flashing of aluminum, gold, or carbon to prevent sample charging.

Figure 5C:
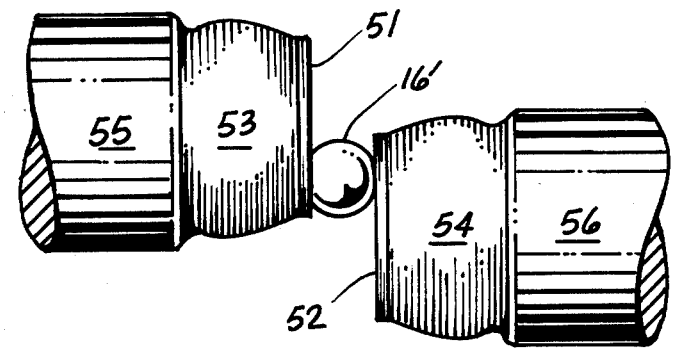

For loading the manipulator, the tips or flat surfaces 51 and 52 of tubes 53 and 54 secured to manipulator arms 55 and 56, for example, are separated slightly (see FIG. 5a) and a sphere 16' is placed between them with a vacuum chuck or other fine probe 57. The manipulator tips 51 and 52 are moved together to frictionally contact the sphere on opposite sides thereof (see FIG. 5b), whereupon the tips 51 and 52 are moved in opposite directions rotating sphere 53 for examination purposes, as shown in FIG. 5c. Experimentally, as pointed out above, the sphere is found to roll without slipping between the tips or flat surfaces so that accurate repositioning and even numerical control of the sphere position can be carried out.

Figure 6:
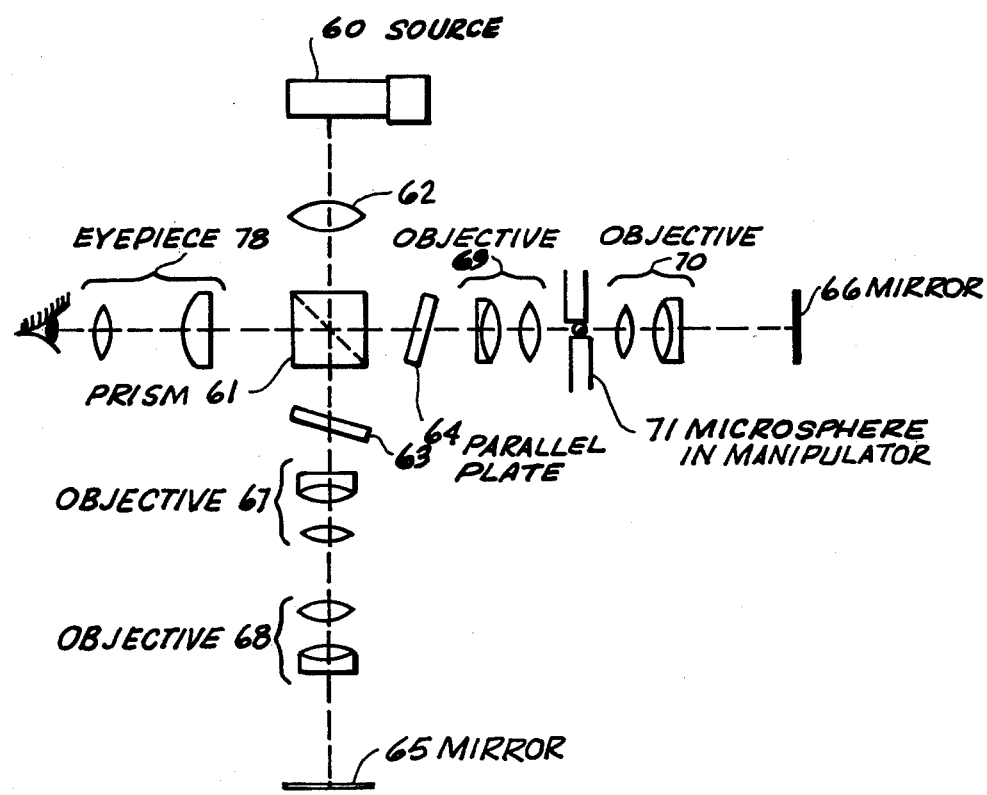
FIG. 6 schematically illustrates a microsphere examination system incorporating the manipulator of the invention.

FIG. 6 illustrates in detail an optical examination apparatus utilizing the manipulator of this invention for retaining and rotating a microsphere, whereby the entire microsphere can be examined with fast repeatably positioning. The apparatus comprises a light source 60, such as white or monochromatic light, which is directed onto a prism 61 via a lens 62, a pair of parallel plates 63 and 64 are positioned at right angles to one another and spaced from prism 61, a pair of mirrors 65 and 66 in alignment with plates 63 and 64, respectively, a first pair of spaced objective lens 67 and 68 positioned in alignment intermediate plate 63 and mirror 65, a second pair of spaced objective lens 69 and 70 positioned intermediate plate 64 and mirror 66 and in alignment therewith, a manipulator 71 containing a sphere to be examined positioned intermediate aligned objective lens 69 and 70, and an eyepiece 78 spaced from said prism 61 and aligned with plate 64 and mirror 66.

It has thus been shown that the present invention provides a simple manipulator for rapidly rotating a sphere or microsphere to any orientation for inspection of the surface and interior thereof. The manipulator is simple, versatile, and useful in many different situations. It can be used in any orientation, can be made quite compact, and requires no precise alignment.

While particular embodiments have been illustrated and/or described, modifications will become apparent to those skilled in the art, and it is intended to cover in the appended claims all such modifications as come within the spirit and scope of the invention.

What is claimed is:

1. An apparatus for rotating a small spherical member about either of two axes without moving the center of the spherical member comprising: a pair of oppositely located members each having adjacent smooth, flat surfaces for retaining an associated spherical member therebetween by substantially frictional contact, and movable means connected to each of said members for moving said members in two directions parallel to said surfaces for rolling an associated spherical member retained therebetween about either of two axes without moving the center thereof.

2. The apparatus defined in claim 1, wherein said movable means consists of a pair of hollow capillary tubes closed at one end so as to form said smooth, flat surfaces and defining said pair of oppositely located members.

3. The apparatus defined in claim 1, wherein said members each consist of a membrane secured to one end of a pair of capillary tubes defining said movable means.

4. The apparatus defined in claim 3, wherein said membrane is composed of a plastic sheet having a thickness of 0.5–20 $\mu$m.

5. The apparatus defined in claim 2, wherein said surfaces each consist of material extruded from the end of said capillary tube and selected from the group consisting of silicone rubber, butyl rubber, urethane rubber, and silicone adhesives.

6. The apparatus defined in claim 2, wherein at least one of said surfaces is provided with a thin flashing selected from the group consisting of aluminum, gold, and carbon.

* * * * *